United States Patent [19]

Suga

[11] 3,983,742
[45] Oct. 5, 1976

[54] LIGHT FASTNESS AND WEATHER RESISTANCE TESTING APPARATUS

[76] Inventor: Shigeru Suga, Yoyogi 5-20-2, Shibuya, Tokyo, Japan

[22] Filed: Dec. 19, 1975

[21] Appl. No.: 642,352

[30] Foreign Application Priority Data
May 8, 1975  Japan.......................... 50-61007[U]

[52] U.S. Cl.................................. 73/15.4; 73/159; 73/432 SD
[51] Int. Cl.[2].................. G01N 17/00; G01N 25/00
[58] Field of Search................ 73/159, 15.4, 432 SD

[56] References Cited
UNITED STATES PATENTS

| | | | |
|---|---|---|---|
| 1,870,512 | 8/1932 | Jameson ............................. | 73/15.4 |
| 2,640,354 | 6/1953 | Bernegger............................. | 73/159 |
| 3,488,681 | 1/1970 | Mita et al. ............................ | 73/159 |

*Primary Examiner*—Donald O. Woodiel
*Attorney, Agent, or Firm*—Wenderoth, Lind & Ponack

[57] ABSTRACT

An improved light fastness and weather resistance testing apparatus has a lamp housing having a closed bottom and sides and an open top, a specimen rack rotatably mounted for rotation around the outside of the lamp housing, a testing vessel around the lamp housing and having a top with an opening therein over the lamp housing and within which the specimen rack is located, and having an inlet port and an exhaust port and a recirculation conduit for recirculating exhaust gas from the testing vessel, gas circulating means and gas humidifying means between the recirculation conduit and the testing vessel inlet, electrode means suspended in the lamp housing and electrode moving means coupled to the upper electrode of the electrode means for raising and lowering the upper electrode. An annular ceiling plate is provided above the lamp housing and spaced from the top of the testing vessel and has a cylindrical wall portion depending therefrom into the lamp housing with the cylindrical wall portion spaced from the edge of the opening in the top of the testing vessel, and an exhaust hood is mounted on the top of the testing vessel over the opening and has a substantially inverted funnel shape with the peripheral edge of the hood on the top of the testing vessel at a position spaced outwardly of the peripheral edge of the ceiling plate. A passage is thereby left from the space within the testing vessel through the space between the cylindrical wall portion and the edge of the opening in the top of the testing vessel and between the ceiling plate and the top of the testing vessel.

2 Claims, 6 Drawing Figures

LIGHT FASTNESS AND WEATHER RESISTANCE TESTING APPARATUS

The present invention relates to an improved light fastness and weather resistance testing apparatus, or fademeter, which artifically reproduces aging similar to exposure to natural conditions to which specimens such as plastics, paints, rubber, fibers, etc., are exposed and which measures the aging within short periods of time.

BACKGROUND OF THE INVENTION

In a conventional weather resistance testing apparatus or fademeter, such as shown in FIG. 1 and FIG. 2, an arc-lmap housing 1 is hung from the top of a test vessel 2 in the center thereof, and a specimen rack 3 which rotates around the lamp housing 1 or shaft 3a driven by a driving means (not shown) is adapted to have a test specimen 4 mounted thereon. Carbon electrodes 5 and 5' at the center of the arc-lamp housing 1 are mounted on holders 6 and 6' which in turn are driven up and down by chains 7, gear mechanism 8 and a motor 9, and the discharge arc is produced between electrodes 5 and 5'. The light produced passes through a light filter 10 and irradiates the sample. An exhaust port 11 is provided at the upper part of the lamp housing to remove high-temperature gases and ashes that are produced during the discharge between the electrodes. The gas in the lamp housing is blown out to the open air by an exhaust blower 12. Cool air is introduced into the lamp housing by being drawn downwardly through two intake pipes 13 on the right and left of the lamp housing and into the bottom of the lamp housing from the lower ends of the introduction pipes.

Thus, the air in the lamp housing is forcibly exhausted. The whirling air creates a disturbed vortex which flows upwardly and into the exhaust port, as can be observed if tobacco smoke or the like is introduced into pipes 13. Therefore, the flame of the discharge arc tends to be oscillated by the disturbance in the air, causing the voltage and current of producing the discharge to become unstable. Furthermore, ashes produced by the discharge arc are carried by the disturbed air stream, scattered and adhered onto the light filter. The ashes adhered onto the filter interrupt the transmission of the light and the amount and intensity of the light energy reaching the specimen tends to be reduced, thereby reducing the effectness of the apparatus for its intended purpose.

The lamp also radiates heat together with light, and the temperature of air in the test vessel rises gradually. To keep the temperature constant, a valve adjusting device including a temperature sensing device 14 is provided in the testing vessel 2, and a change over valve 15 driven by the valve adjusting device is provided between exhaust duct 19 and intake duct 17 to change the air flow pattern to introduce external cool air into the vessel 2 to replace hot air to reduce the temperature. When the temperature in the vessel becomes higher than a set value, the temperature sensing device 14 causes the valve adjusting device to change valve 15 from the position shown by a dotted line in FIG. 2, in which air from vessel 2 is recirculated into duct 17, to the state shown by a solid line. With valve 15 in this position, external cool air is drawn by a blower 16 into duct 17 and blown into the testing chamber 2 after passing through moisture-adding vessel 18. The air introduced into the testing vessel cools the surfaces of the specimen 4 and is forced past the valve 15 and exhausted into open air through exhaust duct 19. The hot air in the vessel is thus replaced by external cool air. When the external air is introduced into the vessel, the pressure created by the blower will be a positive pressure of a few millimeters of water.

The pressure in the lamp housing 1 on the other hand, will be negative pressure due to the suctions being exerted by the exhaust blower 12. Therefore, there develops difference in pressure between the interior of the lamp housing and the testing vessel 2, and the air in the testing vessel 2 flows rapidly into the lamp housing 1 through a clearance between the lamp housing 1 and the light filter 10, as shown by the arrows in FIG. 2, which is a cause of air disturbance in the lamp housing, resulting in unstable discharge. To prevent the occurance of this condition, the filter 10 should have a very flat surface and the surface of the lamp housing to which the filter is attached should be so finished as to maintain close contact with the filter. In practice, however, the heat from the lamp causes bending and sagging of the parts, giving rise to the development of a clearance between them. Therefore, the discharge arc often becomes unstable with each movement of the changeover valve 15. Sudden replacement of air is also a cause of varying air temperature in the testing vessel. The air in the testing vessel usually has a temperature of about 40°C., and even if the temperature of the external air is about 20°C., the introduction of air having a temperature difference of 20°C. causes temperature hunting. This causes a temperature variation, as measured by a blackboard thermometer, of about ±3°C. around 63°C. which is a rough indication of the surface temperature of the specimens.

OBJECT AND BRIEF SUMMARY OF THE INVENTION

The object of the present invention, therefore, is to remove the aforementioned deficiencies inherent in the earlier weather resistance testing apparatus or fademeters.

This object is achieved by the provision of a light fastness and weather resistance testing apparatus having a lamp housing having a closed bottom and sides and an open top, a specimen rack rotatably mounted for rotation around the outside of said lamp housing, a testing vessel around said lamp housing and having a top with an opening therein over said lamp housing and within which said specimen rack is located and having an inlet port and an exhaust port and a recirculation conduit for recirculating exhaust gas from the testing vessel, gas circulating means and gas humidifying means between said recirculation conduit and said testing vessel inlet, electrode means suspended in said lamp housing and electrode moving means coupled to the upper electrode of said electrode means for raising and lowering the upper electrode. An annular ceiling plate is provided above said lamp housing and spaced from the top of said testing vessel and having a cylindrical wall portion depending therefrom into said lamp housing with said cylindrical wall portion spaced from the edge of the opening in the top of the testing vessel, and an exhaust hood is mounted on the top of said testing vessel over the opening and having a substantially inverted funnel shape with the peripheral edge of the hood on the top of the testing vessel at a position spaced outwardly of the peripheral edge of the ceiling plate, whereby a passage is left from the space within the testing vessel through the space between the cylindrical wall portion and the edge of the opening in the top of the testing vessel and between the ceiling plate and the top of the testing vessel. The recirculation conduit has an outside air inlet therein for admitting outside air into the recirculation conduit, and a valve member is provided in said air inlet which is operated for controlling the admission of outside air into the recirculation conduit and through the circulating means and into said testing vessel, said valve member in the closed condition having an edge spaced from the wall of the air inlet for leaving a space through which outside air is drawn when the valve member is in the closed condition.

With this apparatus according to the present invention, carbon arcing is effected under atmospheric conditions and steady-air conditions free of any disturbance of the air, while controlling the temperature by replacing the air in the test vessel with external air. The difference between the pressure in the arc lamp housing and the pressure in the test vessel is minimized so as to make possible stable discharge, and the external air is always introduced in small amounts so that the heat produced by the lamp in the test vessel is conveyed to the external air to stabilize the temperature at the surfaces of specimens. Further the adhesion of ashes to the filter is reduced as compared with the conventional apparatus to prevent the reduction of effect of the arc. Moreover, the apparatus of the present invention is simple and economical to construct.

BRIEF DESCRIPTION OF THE FIGURES

The invention will now be described in greater detail in connection with the accompanying drawings, in which:

As shown in FIGS. 3 and 4, the apparatus of the present invention is similar to that of the prior art as shown in FIGS. 1 and 2, except for the structure of the lamp housing and the exhaust fan 12. Parts which are the same have been given the same reference numbers, such as the rotatable specimen rack 3, shaft 30, test vessel 2, air ducts 17 and 19, circulating fan 16, reservoir 18, electrodes 5 and 5', filter 10, etc.

Figure 1:
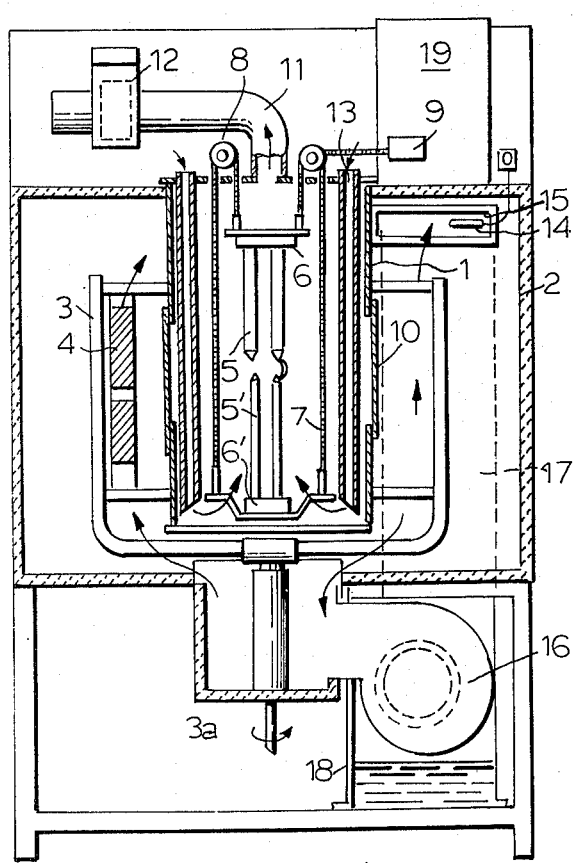
FIG. 1 and FIG. 2 are diagramatic sectional views of a conventional prior art weather resistance testing apparatus or fademeter, FIG. 1 being a front partial sectional view, and FIG. 2 being a side partial sectional view.

The lamp housing 1, has a ceiling plate 20 in the shape of an annular ring with a central opening 21 supported on the top of the testing vessel 2 on posts or supports 22 spaced there-around so that the ceiling plate 20 does not come into direct contact with the ceiling around the opening in the top of the testing vessel 2. A clearance 23 is left between a cylindrical wall portion 20a which depends from plate 20 with the open top of the lamp housing 1 and the edge of the opening in the top of the testing vessel. Further, an exhaust hood 24 is mounted on the top of the testing vessel 2 so as to cover the ceiling plate 20 of the lamp house and the opening in the top of the testing vessel 2. The exhaust hood has an inverted funnel shape, the periphery being tapered and narrowed toward the center. A clearance 25 is also left between the outer periphery of the ceiling plate 20 of the lamp housing 1 and the inner surface of the exhaust hood 24.

Thus the lamp housing 1 is not a closed vessel but is almost completely open at the top, so that the pressure in the lamp housing 1 is substantially equal to atmospheric pressure.

Figure 2:
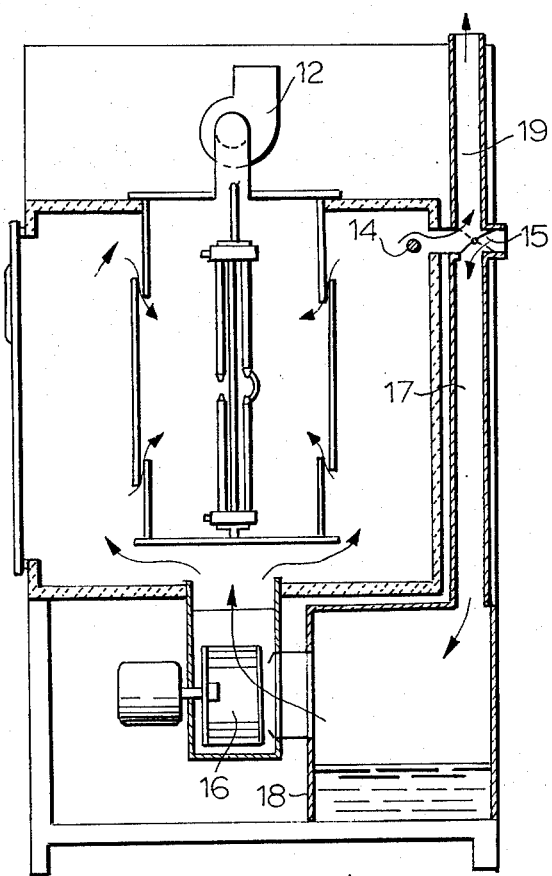

Whereas the prior art apparatus employed an exhaust blower 12, as shown in FIGS. 1 and 2, to exhaust the high-temperature gas in the lamp housing, the present invention employs no exhaust blower 12 or duct 13. According to the present invention, the high-temperature gas produced by the discharge arc rises gradually and is discharged directly to open air due to natural up draft created by the hood 24. That is, the high-temperature gas produced by the discharge of carbon electrodes 5 and 5' rises vertically and goes out directly to open air through the opening 21 in the ceiling plate 20 of the lamp housing and the hood 24. Since the invention employs no forced exhaust system, the pressure in the lamp housing does not become significantly negative and the air therein does not develop unnatural air currents that may disturb arcing; stable discharging voltage and current are maintained.

The prior art apparatus employed a discharge voltage of 50V ± 2% and a discharge currect of 60A ± 2%, but the apparatus of the present invention produces stable discharge at 50V ± 1.5% and 60A ± 1.5%. Further, the high-temperature gas produced by the arcing rises vertically from the center of arcing and the air in the lamp housing flows slowly upwardly from the circumference toward the center of the housing. No such disturbing currents develop which may spread outwardly. Hence, ashes do not move toward the filter in any significant amount and less ashes are adhered to the filter.

With the prior art apparatus, it was common that a new light filter having a transmission factor of 91% had the transmission factor decreased to about 84%, which is a reduction of 7%, after 20 hours use. In the apparatus of the present invention, the transmission factor is decreased to only 87%, which is a reduction of only 4%, after 20 hours of use. This is an indication that very many less ashes are adhered to the filter.

Figure 3:
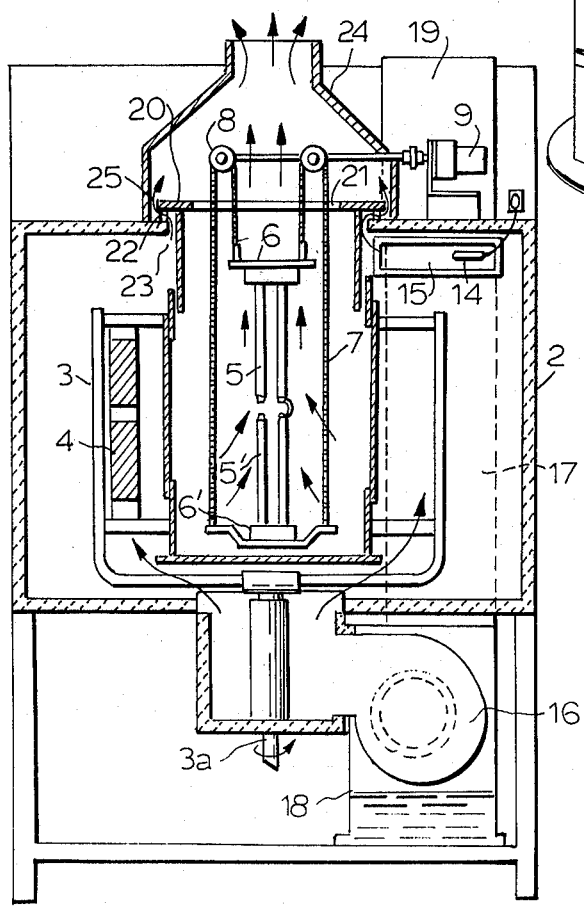

The air in the testing vessel is caused to flow by a circulation blower 16 as in the prior art apparatus through the testing vessel 2 past the air flow changer valve 15, through the circulation duct 17 and the moisture producing means 18 to the circulation blower 16. If the temperature in the vessel exceeds a determined value, the changer valve changes the air flow paths to introduce external air into duct 17. At this time, in the prior art apparatus the air pressure in the vessel 2, was made positive, causing the air to flow into the lamp housing 1 through the gaps along the areas at which the filter 10 is attached to the lamp housing 1, and eventually making the arcing unstable. According to the present invention, however, since the air in the lamp housing 1 is in communication with the external air through clearances 23 and 25, the pressure difference is relieved through the clearances 23 and 25 at the time of the operation of the air controller as indicated by the arrows in FIG. 3. Therefore, the pressure in the lamp housing 1 is not effected and stable discharging is continued. Bending of the filter 10 or the housing 1 where the filter is attached has little affect on the arcing.

Figure 5:
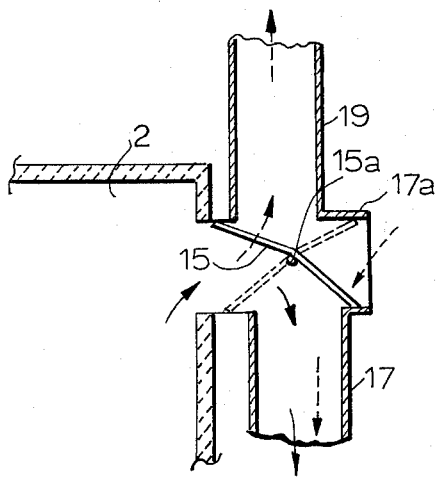
FIG. 5 and FIG. 6 are diagrams to illustrate the construction of an air flow changeover valve in the testing vessel, FIG. 5 showing a conventional valve construction, and FIG. 6 showing a construction according to the present invention.
Figure 6:
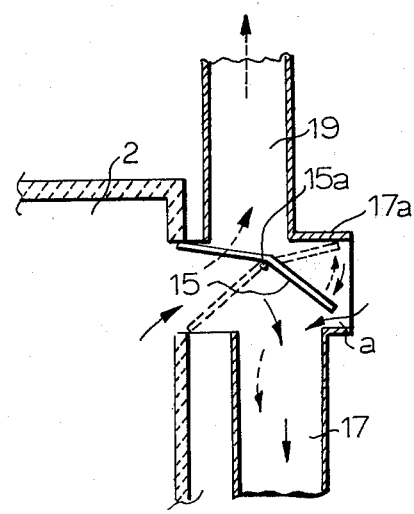
Figure 4:
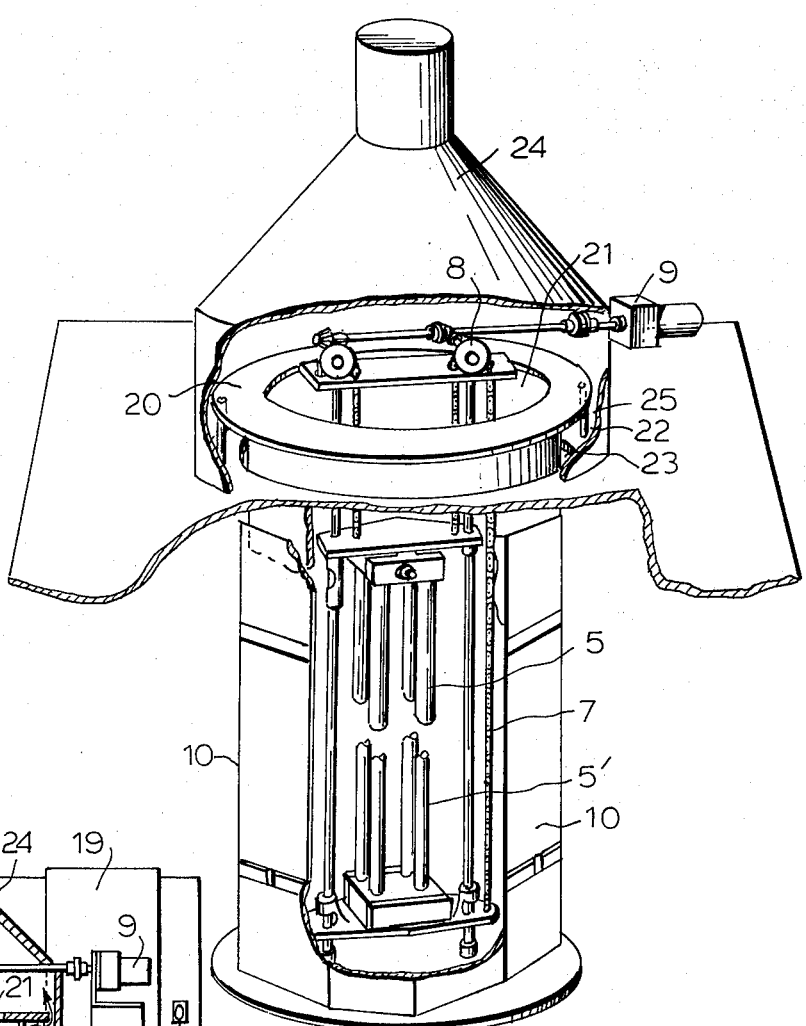
FIG. 3 and FIG. 4 are diagramatic views of an embodiment of the present invention, FIG. 3 being a front partial sectional view and FIG. 4 being a perspective view partly broken away.

The exhaust hood 24 also helps exhaust the high-temperature gas smoothly from the arc lamp which exhaust gas is flowing upwardly at the central part of the housing 1, since the hood acts like a chimney. The exhaust hood further acts to exhaust are from the vessel through the clearances 23 and 25. Moreover, according to the present invention, even when the valve 15 is switched to recirculate the air in the vessel 2, the valve does not shut the passage from the outside air off completely, there is always being provided a clearance $a$ between the valve 15 and the air intake passage so that the external air is not completely shut off; some amount of air is always replaced by external air. That is, with the conventional air flow changeover valve as shown in FIG. 5, when the valve 15 is switched to recirculate air from vessel 2 (flow of air in the conditions is shown by solid line arrows, and the position of valve is shown by a solid line), the valve is completely closed so that no external air will enter through air intake passage 17a. If the changeover valve 15 is changed so that the air from vessel 2 is exhausted and fresh air is drawn in (air flow in this condition is indicated by broken line arrows, and the position of the valve 15 is shown in broken lines), external air is introduced so that the hot air in the testing vessel is exhausted through the exhaust duct. That is, with the prior art changeover valve, either external air was introduced or it was not introduced, to control the temperature in the vessel. Therefore, it was inevitable that temperature hunting was great in the prior art testing vessel. However, according to the present invention, the size of the valve 15 and the position of axle 15a are changed as shown in FIG. 6 so that a clearance $a$ is provided even if when valve 15 is switched to recirculate the air in the testing vessel 2 (the air flow in this case is shown by solid line arrows and the position of valve is shown by a solid line), whereby the vessel is not completely shut off from the external air. Therefore, the air returning to the vessel 2 through the circulation duct 17 is the sum of the air from the testing vessel 2 and the external air entering through the clearance $a$. In this way, cool air flowing through the clearance $a$ absorbs the heat energy radiated from the source of light into the testing vessel 2, and is exhausted into open air via the clearance 23 between the lamp house 1 and the testing vessel, the clearance 25 between the lamp house ceiling plate 20 and the hood 24, and via the hood 24. In this way, since part of air in the vessel is always replaced to take up the heat radiated into the testing vessel 2, the temperature rise is about two-thirds the temperature rise of the prior apparatus. The apparatus of the present invention further develops no temperature hunting. Therefore, although earlier apparatus operated in temperature range of 63° ± 3°C., the apparatus of the present invention operates in a temperature range of 63° ± 1.5°C., which is one-half of the earlier temperature range.

Because part of air in the testing chamber is always being removed, the oxygen concentration in air around the specimen is stable at all times. In testing high molecular weight specimens such as plastics and rubber, such specimens are subject to the synergistic actions of photo-oxidation by the light from the arc lamp and oxidation by air at a black panel temperature of 63° ± 3°C. It is, therefore, very important to continue ventilation so that air will not be deficient in oxygen due to loss of oxygen that is consumed by the oxidation, for the purpose of obtaining reproduceable results.

Since the apparatus has no exhaust blower it is also economical and develops no vibrations due to the electric motor of the exhaust blower; vibration of other precision instruments is reduced, eliminating one cause of troubles, and making the apparatus itself a high precision testing device.

With the prior art apparatus, the removal of air from the testing vessel was conducted for stabilizing the temperature conditions so that they were constant. In other words, if the temperature in the vessel exceeded the set value of the temperature for which the controlling device was set, the air change over valve was actuated to introduce external cool air into the vessel, so that the hot air in the vessel was expelled and the temperature was reduced to a desired level. Until the temperature in the vessel became higher than the predetermined value, the air was recirculated within the vessel.

The increase of the temperature in the vessel depends on the amount of heat which is lost through the walls of the apparatus. In effect, the increase in temperature is determined by the condition of the air in which the apparatus is located. Therefore the temperature gradient differs from the winter season to the summer season. In winter, a larger amount of heat is lost through the outer walls and the temperature increase in the vessel is small. Therefore, the need for ventilation by outside air is reduced. Moreover, because the outside air will have a low temperature, a smaller amount will suffice for lowering the temperature to the desired level.

Quite the contrary thing will hold true in summer. The air circulation which is necessary to maintain the constant temperature condition differs considerably depending upon the outside air conditions when considered in terms of the amount of air replaced.

The conditions are not the same when considered from the standpoint of oxidation by air which acts synergistically with the photo-oxidation. If closed circulation is conducted for long periods of time during winter season, specimens may be exposed to an oxygen-deficient atmosphere.

To maintain such conditions constant, it is necessary to keep the temperature conditions of the place at which the testing vessel is installed constant.

The aforementioned deficiencies were inherent in the prior art apparatus. However, in the apparatus according to the present invention, since the air in the testing vessel is always replaced, that air in the vessel will not lack oxygen, and it is possible to obtain stable and reproduceable results independent of the external air conditions.

As described above, the apparatus of the present invention eliminates drawbacks inherent in the earlier counterparts. Summarized below are the features of the present invention compared with the prior art apparatus.

a. Stability of the source of Light

The prior art apparatus produced a difference in air pressure between the interior of the testing vessel and the lamp housing, which caused air disturbance in the lamp housing; therefore, the discharge was not stable, varying over a range of 50V ± 2% and 60A ± 2% on average.

The apparatus of the present invention, on the other hand, is constructed so that there will be no difference in pressure between the interior of the testing vessel and the lamp housing, therefore, there is no disturbance in the air stream in the lamp housing, and the discharge is very stable, varying within a range of 50V ± 1.5% and 60A ± 1.5% on average.

b. Adhesion of Ashes to the Light Filter

With the prior art apparatus, the turbulent air flow in the lamp housing scattered ashes causing increased amounts of ashes to adhere to the light filter. After 20 hours of use, the transmission coefficient of the filter was decreased by 7%.

On the other hand, with the apparatus of the present invention in which air in the lamp house flows smoothly toward the center of the lamp housing, no ash is scattered and fewer ashes are adhered to the light filter.

After 20 hours of use, the transmission factor of the filteer is decreased by only 4%.

c. Smoothness of the contact surface of the Light Filter

In the prior art apparatus, the filter had to be finished smooth where it contacted the lamp housing so that no air would flow through the spaces between the filter and the filter-mounting surfaces on the wall of the lamp housing.

According to the apparatus of the present invention, on the other hand, even some bending of the light filter does not affect the stability of the source of light.

d. Temperature Control in the Testing Vessel

With the prior art apparatus in which hot air in the testing vessel is replaced all at one time by outside air by switching the change over valve, hunting develolped over the range of 63° ± 3°C., i.e., ± 3°C. as measured by a blackboard thermometer.

In the apparatus of the present invention, on the other hand, in which part of air in the testing vessel is always being replaced by the improved changeover valve mechanism, the range of hunting is decreased to 63° ± 1.5°C., i.e., ± 1.5°C as measured by a blackboard thermometer.

e. Stabilization of Photo-Oxidation Conditions

Prior art ventilation consisted of a repetition of a condition in which the changeover valve was open to permit drawing in of outside air, and a condition in which the change over valve was closed to cause closed circulation; the time of ventilation varied depending upon the external air temperature, often resulting in an oxygen-deficient atmosphere during closed circulation. Therefore, the conditions were not constant.

In the apparatus of the present invention, on the other hand, part of the air is replaced at all times with enough air being supplied to the specimens so that atmospheric conditions related to the photo-oxidation are stabilized.

f. Vibration due to the Exhaust Blower

The prior art apparatus employed an exhaust blower to forcibly exhaust air from the lamp housing; the resulting vibration effected other precision instruments.

The apparatus of the present invention, on the other hand, employs no exhaust blower and is free from such vibration and possible troubles caused thereby. The present invention provides a high-precision and economical apparatus.

What is claimed is:

1. In a light fastness and weather resistance testing apparatus having a lamp housing having a closed bottom and sides and an open top, a specimen rack rotatably mounted for rotation aaround the outside of said lamp housing, a testing vessel around said lamp housing and having a top with an opening therein over said lamp housing and within which said specimen rack is located and having an inlet port and an exhaust port and a recirculation conduti for recirculating exhaust gas from the testing vessel, gas circulating means and gas humidifying means between said recirculation conduit and said testing vessel inlet, electrode means suspended in said lamp housing and electrode moving means coupled to the upper electrode of said electrode means for raising and lowering the upper electrode, the improvement comprising an annular ceiling plate above said lamp housing and spaced from the top of said testing vessel and having a cylindrical wall portion depending therefrom into said lamp housing with said cylindrical wall portion spaced from the edge of the opening in the top of the testing vessel, and an exhaust hood on the top of said testing vessel over the opening and having a substantially inverted funnel shape with the peripheral edge of the hood on the top of the testing vessel at a position spaced outwardly of the peripheral edge of the ceiling plate, whereby a passage is left from the space within the testing vessel through the space between the cylindrical wall portion and the edge of the opening in the top of the testing vessel and between the ceiling plate and the top of the testing vessel.

2. The improvement as claimed in claim 1 in which said recirculating conduit has an outside air inlet therein for admitting outside air into the recirculation conduit, and said improvement further comprises a valve member in said air inlet which is operated for controlling the admission of outside air into the recirculation conduit and through the circulating means and into said testing vessel, said valve member in the closed condition having an edge spaced from the wall of the air inlet for leaving a space through which outside air is drawn when the valve member is in the closed condition.

* * * * *